United States Patent [19]

Brodard

[11] Patent Number: 5,285,781
[45] Date of Patent: Feb. 15, 1994

[54] ELECTRICAL NEUROMUSCULAR STIMULATION DEVICE

[75] Inventor: Roland Brodard, Villeneuve, Switzerland

[73] Assignee: Stiwell S. A., Switzerland

[21] Appl. No.: 705,078

[22] Filed: May 24, 1991

[30] Foreign Application Priority Data

May 26, 1990 [CH] Switzerland ............... 1781/90
Dec. 20, 1990 [CH] Switzerland ............... 4066/90

[51] Int. Cl.$^5$ ............................................... A61N 1/36
[52] U.S. Cl. ............................................ 607/59; 607/66
[58] Field of Search ................... 128/421, 422, 423 R

[56] References Cited

U.S. PATENT DOCUMENTS

| | | | |
|---|---|---|---|
| 4,254,776 | 3/1981 | Tanie et al. ............. | 128/421 |
| 4,672,769 | 2/1987 | Petrofsky ................. | 128/421 |
| 4,919,139 | 4/1990 | Brodard ................... | 125/421 |
| 5,036,850 | 8/1991 | Owens ...................... | 128/421 |

FOREIGN PATENT DOCUMENTS

197889 10/1986 European Pat. Off. .
316280 5/1989 European Pat. Off. .

*Primary Examiner*—William E. Kamm

[57] ABSTRACT

An electrical neuromuscular stimulation comprising at least one stimulation unit, which is portable and autonomous, controlled by a detachable and interchangeable information medium, previously programmed as a function of the treatment for each respective patient, equipped at its output with at least one pair of electrodes designed to be applied to the part of the patient's body to be treated and to transmit trains of electrical stimulation impulses intended to cause contractions and muscular exercise or training, said stimulation unit comprising an electronic circuitry (hardware) of the amorphous type, under the supervision of a control software with interactive parameters and linked by coupling and interaction functions, with said software being memorized on the detachable information medium, with it being possible for the value of each parameter to evolve progressively throughout the program between previously programmed reference values, and any parameter being able to control another parameter.

28 Claims, 7 Drawing Sheets

ELECTRICAL NEUROMUSCULAR STIMULATION DEVICE

The present invention relates to an electrical neuromuscular stimulation device.

Electric neuromuscular stimulation consists in a transcutaneous transmission, by the bias of surface electrodes, of very weak electrical impulses to the nerve and/or to the appropriate muscle so as to cause its excitation. The excitation achieved is identical with that which is normally caused by an autogenous physiological nervous impulse.

Depending on the intensity of the impulses and in particular on their distribution pattern as a function of time, two fundamental options may be defined: either an antalgic action, or a muscular motor action (muscular contraction), called electromyostimulation. Electromyostimulation is in turn divided into two distinct branches, that of the healthy muscle, normally innervated, and which is thus a functional electromyostimulation, and that of the peripherally enervated muscle, which requires stimulation parameters and a method of application totally different from the above.

The essential objective of electromyostimulation is to serve as a substitute for a temporary or permanent deficiency in voluntary muscular activity, so as to overcome its consequences, or at least to lessen them, and to reduce as much as possible the recuperation time of voluntary activity.

The principle of electric neuromuscular stimulation is not recent. In 1791 the scientist Luigi Galvani laid the foundations for it by his successful experiments involving the electrical stimulation of a frog's muscle. From that time and in actual fact until present, very little progress has been made in electrostimulation. Experiments have been essentially performed with different types of stimulation current, to which doubtful and deceiving therapeutic virtues have been attributed and which were only supported by empirical observations.

However, during the last ten years the study of the physiology of the muscle has made rapid strides. It has been discovered that the skeletal muscle is an extremely plastic, heterogenous and adaptable tissue.

The different types of fiber which comprise a muscle have been arbitrarily and very diagrammatically split into two basic groups:

Type I fibers, with slow contraction, not very powerful, but resistant to fatigue. These fibers have a postural function and are also stressed during a sports-related endurance activity.

Type II fibers, with fast contraction, strong but subject to fatigue. These fibers are greatly involved in sports-related strength activities which are comparatively short.

These two types of fiber operate in different and specific contraction frequency ranges. Thus the operational frequency range of the type I fiber extends over a range in the order of 8 to 25 Hertz, whereas that of the type II fiber extends over a range of approximately 25 to 65 Hertz.

However, taking into consideration the most recent findings in muscular physiology, such a classification of fibers has proved to be much too brief and arbitrary. In fact, the large differences in the functional muscular activity developed during everyday life suggest the need for a much wider variability of metabolic profiles, in different muscular fibers. The reality of this has now been demonstrated by the ultramodern histochemical analysis methods, which have enabled analysis to be improved and a fine and precise enzymatic quantity determination to be established within each muscular fiber.

It has thus been possible to show that any given functional requirement determines a muscular contraction characterized by four parameters: its force, its speed, its duration and its repetition frequency.

The combination of the various values taken by these parameters will consequently solicit one of the three following routes for the energetic metabolism of the muscle concerned: the aerobic route, the alactic anaerobic route or the lactic anaerobic route. Since the morphological (structural) and metabolic (biochemical) profiles of a muscular fiber, which are suitable for ensuring an aerobic route or, in contrast, an anaerobic route, diverge considerably, it follows that not only there is no single and universal type of fiber within the muscle, but it is also established that the muscular fibers can not be rigidly classified into the two types described above.

On the contrary, the muscular fibers form a continuous spectrum of fibers, with different levels of metabolic organisation adjusted to a large range of functional requirements. Moreover, the muscular tissue is permanently in dynamic equilibrium between a degradation (catabolism) and a new synthesis (anabolism). This same dynamic equilibrium governs the morphology and the metabolic profile which characterise each of the phenotypes of the muscular fibers comprising a given muscle. It is this same dynaminc equilibrium which imparts to the muscle its extraordinary plasticity: although the initial distribution of the different muscular fibers within a given muscle is of genetic origin, this distribution is not rigid, but it may be modified, as much by a crossed innervation as by a constant specific functional requirement imposed on the muscle or even by chronic electromyostimulation. Consequently, the phenotype of a muscular fiber is determined by a set of adequate responses to constant functional requirements. Certain predominant plans of use for locomotion or posture should favour the expression of certain predominant phenotypes.

In view of the above considerations, it is not surprising that the muscle contains a spectrum of fibers amongst which certain kinds form limited populations, constituting metastable entities, corresponding to the types of fibers generally described until then.

It has thus been possible to show on the basis of recent knowledge about muscular physiology that the very real efficiency of electromyostimulation is a direct function of the degree of mimesis which it respects of the equivalent voluntary activity for which it acts as substitute.

On the other hand, the traditional weekly or twice weekly courses of electrotherapy, have today been totally replaced by daily treatment programs of longer duration. Such a daily stimulation implies that the patient himself assumes responsability for the treatment whether in hospital or at home, under periodic medical supervision.

Already known are electrical neuromuscular stimulation installations comprising a programming appliance and a stimulation appliance operating independently of one another. The programming appliance for these installations is designed to record a program of treatment on a read only memory information medium, with this information medium which contains the program being placed in the stimulation appliance to control it and to perform the program. Such installations are described, for example, in French patent No. 1213080, in published German patent application No. 2903392, in published European patent application No. 0087617 and in published French patent application No. 2528709.

The major drawback of these installations is that they are designed with static memories, i.e. that the programmed stimulation parameters are fixed and do not vary as a function of the treatment time. For this reason, throughout the entire treatment, the muscle is subjected to a uniform and constant metabolic regime, with none of the appliances described in these publications making allowances for the physiological conditions mentioned above and which have to be observed so as to obtain an effective muscular training which is exempt from a deterioration of the muscular tissue.

A more advanced installation, which comprises a programming appliance (also designed to record a program of treatment on a detachable information medium, but with a random access memory), which can work on-line with a stimulation appliance is described in published European patent applications Nos 0197889 and 0316280. The technique revealed in these patent applications is based on a now out-dated work hypothesis, which is based on the above-mentioned distinction between "slow" muscular fibers and "fast" muscular fibers. This installation is designed for sequential programming, with it being possible to divide the duration of a treatment into a certain number of distinct sequences, with it being possible to program each so as to generate trains of electrical impulses, the characteristics of which are adapted to the slow muscular fibers, and other trains of electrical impulses, the characteristics of which are adapted to fast muscular fibers.

The major drawback of the installation described in these two European patent applications is that the value of each programmed stimulation parameter remains fixed within each sequence and that this value may only be brutally altered at the time of the switch from one sequence to another. Such brutal variations, which have no transitional stage from one specific regime of muscular work to another, scarcely reflect real patterns of voluntary muscular activity in everyday life.

This drawback even means a major risk of damage to the tendino-muscular tissue, when it is known that the intensity of the force produced by a muscular contraction is the result of the following physiological phenomena:

1) the intensity of the force is a function of the number of motor units which are enlisted and therefore stimulated at a given moment: this is the "spatial summation", a function of the intensity of the electrical stimulation current;
2) the intensity of the force is also a function of the frequency of the stimuli of a given motor unit: this is the "temporal summation".

It is known that between a simple series of separate muscle jerks at low sub-tetanic frequency (for example at 8 Hertz) and a frequency determining a complete tetanic fusion (for example at 25 Hertz for type I fibers and at 65 Hertz for type II fibers), the force supplied for a same intensity of electrical stimulation current increases according to a factor of 4 to 5.

It is precisely for this reason that, in the above-mentioned installation, when the programmed frequency increases between two consecutive sequences, the switch from one sequence to the next can not be automatic: the progress of the treatment is then interrupted, while the electric current is automatically cut. The user is then forced to restart treatment at the beginning of the following sequence and to readjust the intensity of the current as a function of the new programmed frequency, so as to determine a tolerable intensity of the force supplied by the new type of muscular contraction. This procedure is more especially tiresome as the program is multi-sequential.

It is now known that, at the time of a voluntary development of the muscular force, there is interaction and connection between the spatial summation and the temporal summation described above. Very schematically, one can say that as a function of the initial force to be developed, a certain number of motor units are simultaneously enlisted and contract at a given frequency; then progressively as the force supplied increases, the said frequency rises and new additional motor units are enlisted, whereas the contraction frequency of all the motor units enlisted continues to increase. It is noted however that in this complex mechanism of interaction and connection of spatial and temporal summations, the former remains predominant in comparison with the intensity of the force supplied by the muscle.

On the other hand, for physiological reasons, which go off the present invention, the different outputs towards the electrodes of a multichannel output stimulator should always be electrically independent, i.e. galvanically insulated between one another and the earth and consequently called floating. This requires the use of an insulation device in which the voltage of the stimulator is uncoupled from the earth. Generally this device is formed by a transformer. However, bearing in mind electrophysical properties of a transformer, the length of transmission of a constant current rectangular impulse can hardly be extended past 400 microseconds, even at the expense of better quality and of an increase in the volume of said transformer. This restriction considerably limits the performances of the electrostimulation which can not consequently be applied to muscles which are peripherally innervated, the stimulation of which imperatively requires impulses of a duration of between 300 and 500 milliseconds.

Up until now, none of the known independent, portable multichannel stimulators met the conditions given above, so as to be able to stimulate both muscles normally innervated and also muscles which are peripherally enervated.

The object of the present invention is to propose an electrical neuromuscular stimulation device, in the form of a miniaturised portable autonomous appliance, which avoids the faults which have just been listed and which satisfies the demands which the latest knowledge acquired in neuromuscular physiology have shown to be necessary so that the electromyostimulation ensures the closest mimesis of voluntary active muscular training, whilst retaining one of the simplest applications, guaranteed by an advanced automatism.

For this purpose the invention relates to an electrical neuromuscular stimulation device, such as defined in claim 1.

Other important characteristics of the invention are defined in the claims subordinate to claim 1.

The advantages of the invention will be cleary illustrated by the following description, given by way of example, and which refers to the attached drawings.

Figure 1A:
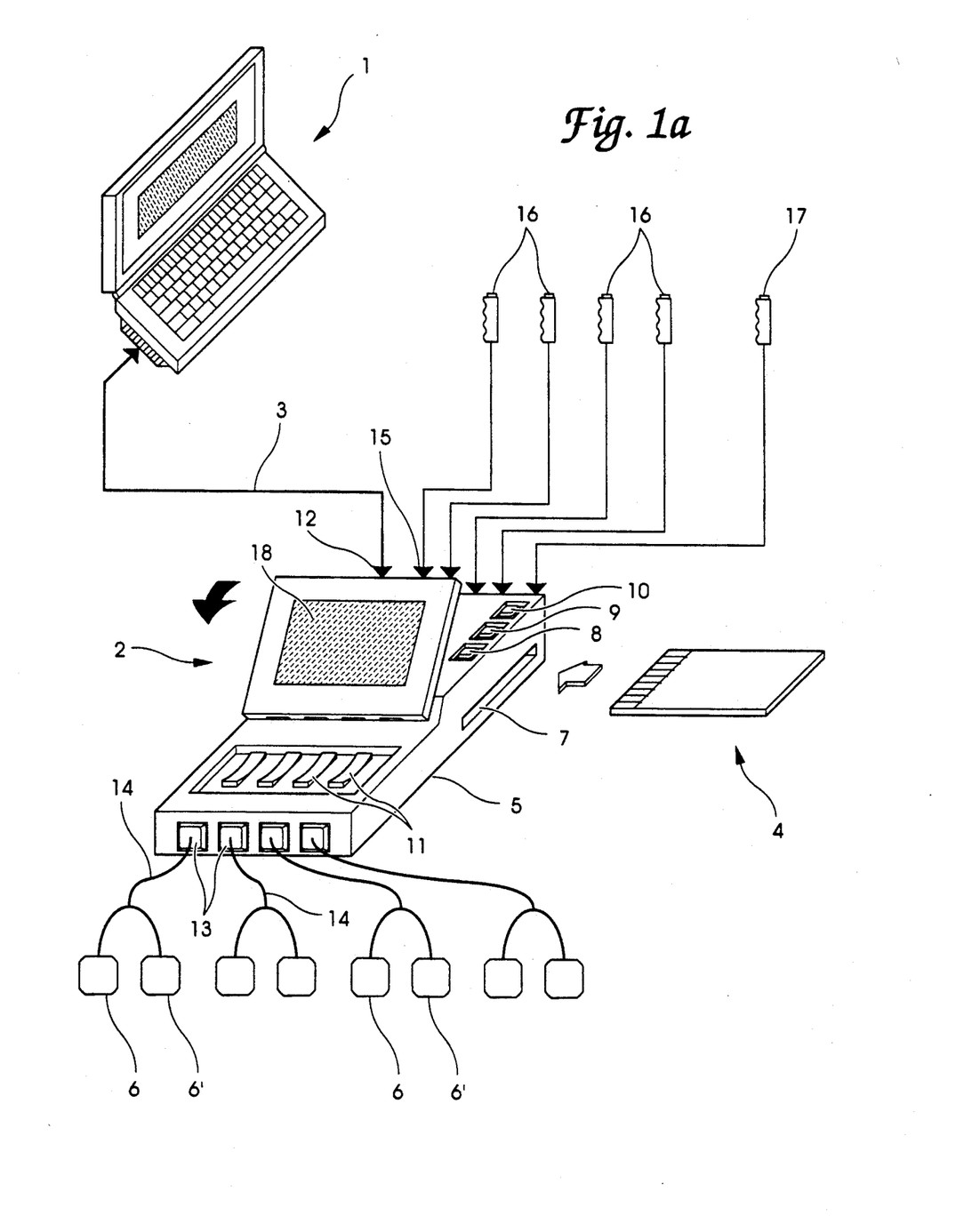
FIG. 1a is a diagrammatic general perspective view of a first embodiment of the device, comprising a stimulating unit 2 and a computer 1 connected by a detachable cable 3.

The device shown in FIG. 1a comprises a commercial computer 1 and a stimulation unit 2 connected by a detachable cable 3 ensuring an on-line RS-232C serial link. The stimulation unit 2 is portable and independent. It is controlled by a detachable and interchangeable information medium 4, which can be beforehand programmed as a function of the treatment required by each respective patient. The stimulation unit is designed according to a concept of the miniaturised walkman style. Its housing 5 contains the component, mechanical and electronic parts. It is equipped with four pairs of electrodes 6, 6', designed to be applied to the part of the patient's body to be treated and so as to transmit the trains of electric stimulation impulses.

The outside of the housing 5 is designed so as to make the following units available to the user:
- an LCD display screen 18 of the dot matrix type, which can be folded back so as to form a protective cover, functioning in TV mode and controlled as much by the operating software as by the software constituting the program of treatment. Such a device, which displays both alphanumeric characters and also graphical images, enables all the functions of the appliance and of the stimulation to be monitored, such as stimulation parameters, length of treatment, charging condition of the batteries, bar graphs showing the intensity of the stimulation current at each output, form of impulse used, observance (compliance) with the treatment by the patient, identification of the program of treatment loaded on to the information medium connected to the appliance, instructions of use to the patient, etc.,
- a general switch 8 for the operation of the appliance,
- a control 9 for starting and temporarily interrupting the treatment,
- a control 10 for the temporary suppression of the period of rest,
- controls 11 which enable the intensity of the stimulation current at each output to be increased or reduced,
- a connector 12 enabling the detachable multi-fonction cable to be connected, thus ensuring the link with the battery charger or with an external standard mutual control device, or even the on-line serial link with a computer,
- a slot 7 having a connector 23 for the detachable and interchangeable information medium 4,
- connectors 13 provided to connect cables 14 for each pair of electrodes 6, 6', as well as connectors 15 corresponding to the latter for the individual external control 16 of each output.

The stimulation device 2 is equipped with a slot 7 and a connector to receive the memory card, as well as with a connector having a detachable cable 3 enabling a type RS-232C serial link. The stimulation device may therefore be immediately connected to any computer fitted with a type RS-232C serial interface. It therefore has the decisive advantage of avoiding the necessity for any specific programming appliance.

To load any software (operating software or program of treatment) onto a memory card, one only has to connect the latter to the stimulator by placing it in its slot and connecting said stimulator by its RS-232C serial link to an adequate computer. Then, by means of said computer and the on-line serial link thus established, one can choose from the following:
- to transfer an operating software from the computer onto the memory card and simultaneously into the internal memory of the stimulator,
- to transfer a software constituting a program of treatment onto the memory card,
- to perform the free programming of a program of treatment by means of the computer and simultaneously to load this program onto the memory card,
- to modify an existing program of treatment, previously transferred onto the memory card, as an on-line function, i.e. in real time during the actual course of said treatment on the patient.

Memory cards, already loaded with a software in conformity with one of the procedures mentioned above, may of course at any time be connected to a stimulator and used by the latter either in an absolutely independent way, or in an on-line serial link with the computer.

It will be noted that the serial link authorises a true bi-directional dialogue, called read-write, between the computer and the stimulator. In the computer-stimulator direction, it enables the transfer of software and of parameters and data intended to then be processed by said software; whereas in the stimulator-computer direction, it enables software already transferred to be reread, and also parameters and data memorised on the memory card connected to the stimulator. An example of this is provided by observance, in which the retro-control data provided by the stimulator during the progress of the program of treatment are memorised on the memory card.

The stimulator comprises a connector having a detachable cable ensuring the link with a device for the standard external control 17 common to all the outputs and which enables the start or finish of a given function, defined by the software, to be monitored globally. Furthermore, besides this general function, it comprises connectors 15 advantageously provided for the individual control 16 of each output channel. This individual control enables, by the bias of the specific program loaded into the appliance, to control the beginning or the end of the function of the appropiate channel and also to remote-control the intensity of the force of the contraction, by acting on the intensity of the current and the impulse frequency. The connection of this control to an adequate external pick-up permits the transmission of information to the software of the appliance and to ensure, for example, a correct functional training of the activity of the patient's limbs, on the basis of data provided by this retrocontrol (feedback and closed-loop control).

Figure 1B:
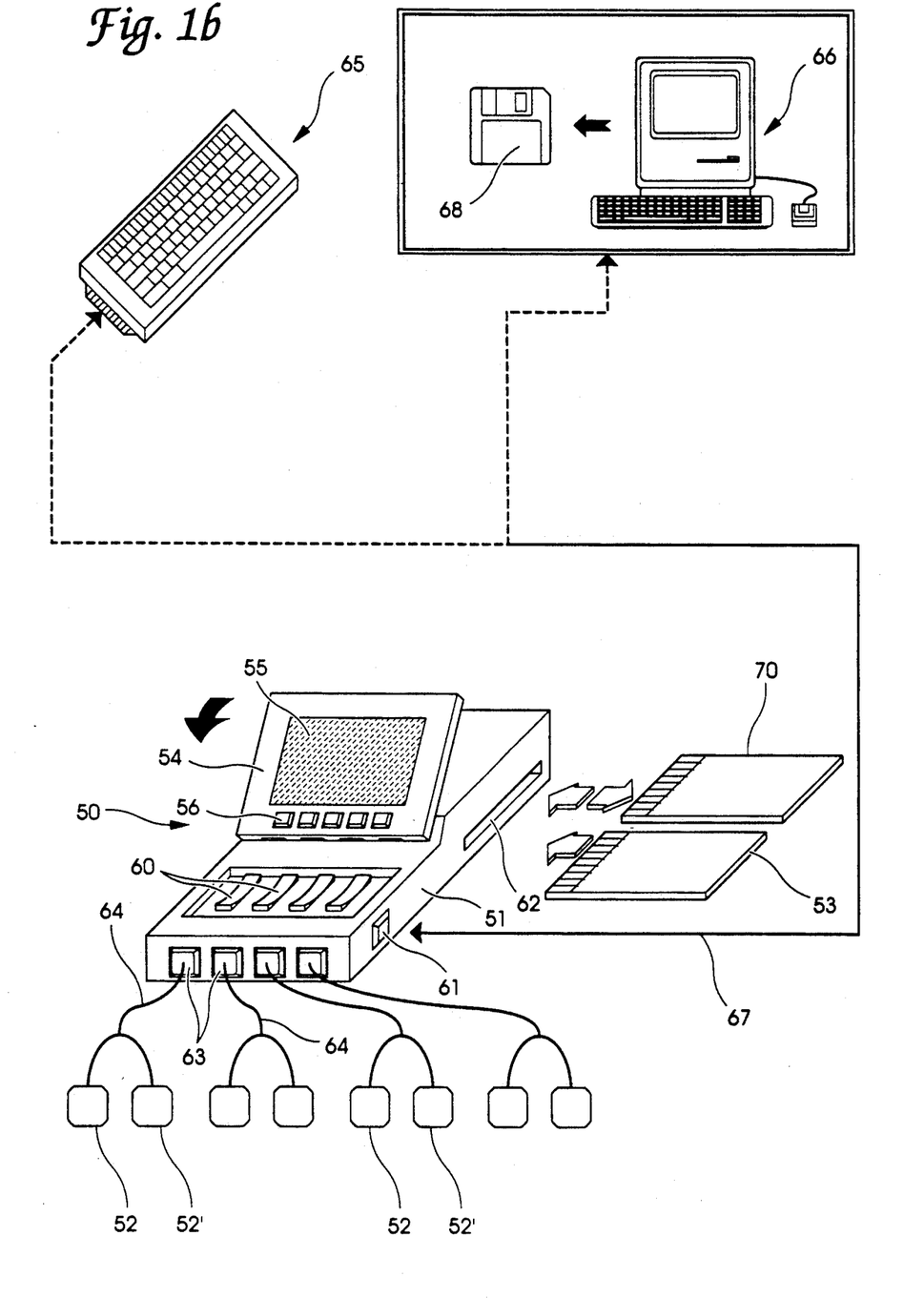
FIG. 1b is a diagrammatic general perspective view of a stimulation unit 50 according to a second embodiment of the device, and its connection with optional peripheral units.

According to a second embodiment, shown on FIG. 1b, the device comprises a portable and autonomous stimulation unit 50, designed so as to enable a simple personalisation of any parameter by means of function keys 56, enabling the computer 1 described above to be dispensed with. Just like the stimulation unit 5 shown in FIG. 1a, this unit is contructed according to a concept of the miniaturised walkman style. Its housing 51 contains the component, mechanical and electronic parts. It is equipped with four pairs of electrodes 52, 52' designed to be applied to the part of the patient's body to be treated so as to transmit the trains of electric stimulation impulses. The stimulation unit is controlled by a detachable and interchangeable information medium 53, beforehand programmable as a function of the treatment required by each respective patient. The exterior of said housing 50 is designed so as to make the following units available to the user:

- a dot matrix LCD screen 55, similar to screen 18 of the stimulator shown in FIG. 1a;
- function keys 56 (five in the example shown in FIG. 1) with fugitive action, subordinate to the software. One temporary specific function is assigned to each of them as required, with it being possible to display this function on a reserved portion at the bottom of the screen;
- the screen 55 and the function keys 56 are disposed on a unit 54 which can be folded back so as to form a protective cover;
- rocker controls 60 enabling the intensity of the stimulation current of each output to be increased or decreased gradually;
- a multi-function connector 61 intended to receive a detachable cable 67, which enables it to be connected with the battery charger or an auxiliary power supply battery for treatments lasting a very long time, or with a keybord 65, a computer 66 or any other control device, or even the switching of several stimulators in network;
- a slot 62 having a connector for the detachable and interchangeable information medium 53;
- connectors 63 provided to connect cables 64 for each pair of electrodes 52, 52'.

The stimulator 50 is designed so that its bringing into service is effected by means of one of the function keys 56. For example, the interlocking function may be assigned to any one of the function keys, with this key becoming available again for another function after interlocking. It could also be stipulated that the bringing into service of the stimulator is effected when any function key is pressed. But of course this bringing into service may also be effected in any other satisfactory way. Furthermore it may also be stipulated that the command to trigger and temporarily interrupt the treatment and the command for the temporary suppression of the rest period are carried out with the help of a function key, the number of which is indicated on the screen, for example on its lower part.

Regardless of whether it is constructed according to the embodiment shown in FIG. 1a or according to the embodiment shown in FIG. 1b, the present device enables the activity of the different output channels, which can be programmed independently of one another, to be made interdependent as required, with it being possible to make each parameter of one output channel subordinate to another output channel. This authorises the programming of multiple, synergist, alternating synergist/antagonist or complex relayed muscular activities.

Figure 2:
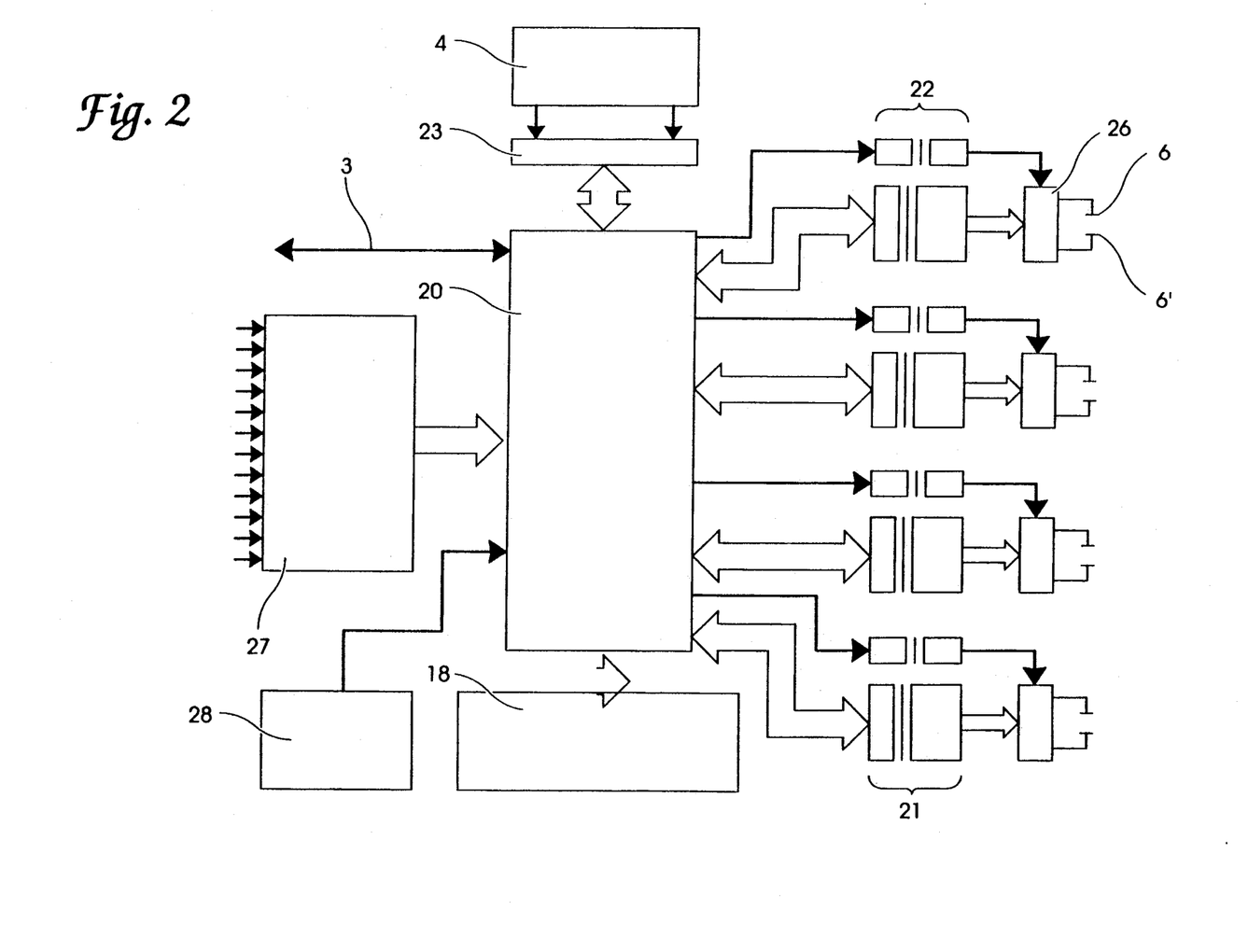
FIG. 2 is a block diagram of the stimulation unit of FIG. 1.

As shown on the block diagram in FIG. 2, regardless of which embodiment described above is used, the electronic circuitry (hardware) essentially consists in a true microcomputer 20 which generates electrical impulses. This microcomputer is formed of the traditional units: processor, ROM and RAM. This micro-computer is served by an input interface 27 for the manual commands and external commands.

From the original form of the programmed impulse (for example, a rectangular impulse of constant current or a triangular impulse of progressive current), the microcomputer calculates and supplies high frequency impulses to a true installation cell 21 comprising an inductive transmitter and a demodulator, with the latter comprising a full-wave rectifier and a filtering and smoothing cell, so as to form an output pulse shaper of the stimulation current towards the electrodes; i.e. that the high frequency signal thus obtained is then transmitted and amplified (boosted) inductively, independently for each output; then this signal is rectified, filtered, and smoothed so that the original programmed form of the impulse at the output of this circuit is again restored.

However, as such a rectified impulse is by necessity supplied with a constant polarity, the rectifier stage has been supplemented by an electronic polarity throwover switch stage 26, controlled by the software, via an electrical insulation cell 22, formed by a transformer or an optocoupler.

Figure 3:
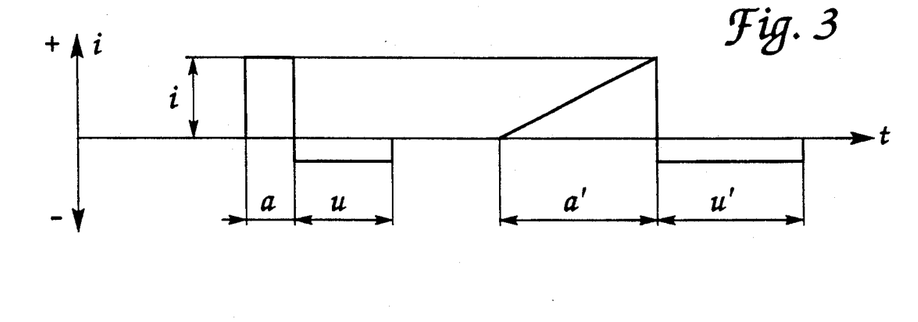
FIG. 3 illustrates, by way of example, two distinct forms of impulse, showing the variation in its amplitude i as a function of its duration a, a'.

This method has the advantage of allowing the supply of impulses of constant current or having a variable slope, as shown on FIG. 3, programmed for any length of time, or even for the provision of a true uninterrupted direct current, intended for ionotherapy, whilst retaining a permanent check on the polarity of the output current, which moreover and in particular authorises to produce asymmetrical impulses, which are also designated as being compensated, because the flow of current of the active stimulation impulse a, a' is then totally compensated by an inverse flow of current u, u' of lower inactive but prolonged intensity, with the major advantage of a balancing (zero medium flow) of the electrical charges at skin level, which is imperative to warn of any burn or electrolytic deterioration of the latter.

This general design has the advantage that all the electronic circuitry (hardware) is of the amorphous type, i.e. is entirely under the control of the software, which ensures maximum flexibility in use and in the adaptation of the system.

The system operates by means of two distinct software programs, that is to say a system or operating program and a treatment program, with the latter constituting the program of treatment in the proper sense of the word, which is loaded and memorised on the detachable and interchangeable information medium 4, respectively 53, with each program of treatment thus constituting a different application program. The operating program may be loaded into a live internal memory of the appliance, of the RAM type, where it remains permanently until its possible replacement when another operating program is loaded. However, according to a preferred embodiment, the stimulator does not comprise any residential memory, the operating software being also memorised on the detachable and interchangeable information medium, from where it is in permanent dialogue with the microprocessor.

The electronic circuitry is supplied by rechargeable cells or batteries 28, incorporated into the housing 5, respectively 51.

The control of the intensity of the stimulation current for each output is generally carried out by means of a potentiometer or two temporary action keys, with one (+) being intended to increase this intensity, whereas the other (−) decreases said intensity.

With the present device, since the intensity of the current, assigned initially by the therapist, is memorised by means subordinate to the program and to the processor, the manual control 11, respectively 60, of the intensity is in fact a supplementary control, essentially used to correct if necessary the programmed intensity. Such a control consequently also acts by means subordinate to the program and to the processor.

The control device for monitoring the intensity of each output is a single rocker switch 11, respectively 60, having temporary action. In its position of rest, it is in the inactive neutral state. The advantage of this device is that it only requires for its operation the use of a single finger and that it thus allows a precise and fast adjustment of said intensity by a simple slight displacement of this finger on the key.

It is obvious that the detachable and interchangeable information medium may be realised in different ways. In the example described here, it concerns an element called a microchip card 4, respectively 53, having the format of a credit card, containing live memories of the EEPROM type (electrical erasable programmable read only memory) or RAM (random access memory) and fitted with a connector. This memory card operates like a computer diskette.

The device is designed for a freely developing dynamic programming with interactive parameters. The microcomputer of the stimulator comprises a system of internal reference clocks, to which the programs used are subordinate. By this design, the user has an entire capacity of free programming for all the stimulation parameters as a function of the performance time of the program of the treatment; this programming, which is a function of time, is both provided for the introduction and utilisation of a given parameter then its eviction, and for the value which is assigned thereto.

To facilitate programming and to ensure a suitable progressiveness of the variation of the value assigned to a given parameter as a function of time, it is ensured that the user may freely fix, by sampling as a function of time, the value assigned to this parameter, either arbitrarily by referring to his knowledge and experience, or experimentally by using the on-line serial link with the computer or the function keys and by initialising the value of said parameter in real time during the effective progress of the program of treatment on the patient, and therefore as a function of the reactions of said patient.

Since the programming of the stimulator is freely developing dynamic programming with interactive parameters, it results that, as a function of the progress of a program of treatment, the value of any stimulation parameter may evolve continously and progressively between previously assigned reference values, whereas any given parameter may bring another under its control.

The frequency of the impulses may thus for example continuously and progressively pass from a completely subtetanic regime to a completely tetanic regime, whereas the intensity of the corresponding output current, subordinate to the frequency, is consequently corrected and adapted, also continously and progressively, to keep the muscular force produced within quasi constant or previously defined values.

Such a programming enables programs of muscular exercise to be performed which observe a continuous and gradual progression in the intensity of the muscular activity developed, copied from the physiology of similar voluntary training. The value of this condition is emphasized when performing a series of contractions, such as, for example, during a staggered training program.

The connector 61 of the stimulator in FIG. 1b may be used to effect a data link of the data bus type which enables the interactive external remote control of the output channels of one or several stimulators coupled in network. In the latter case, the link may be effected by a multiple serial star line, having a central point, with it being possible to form the central point by a computer or any other control device, or by one of the stimulators into which a master patient card has been inserted, to which card the patient cards of the other stimulators are subordinate.

In the case of the stimulator shown in FIG. 1b, the stimulator may be programmed with the help of beforehand established program cards 70, which are servers for standard treatment programs, with each program being specific to a precise given medical indication. When this card is introduced into the slot 62, a list of programs appears on the screen and a standard program may then be chosen, either with the help of the function keys 56, or with the help of a keyboard 65, a computer 66 or any other control device which can be connected to the stimulator by means of line 67. The chosen program may then be copied onto a blank patient program card which is introduced into the slot 62 after having withdrawn the program card 70. The chosen program may then be easily personalised and adapted to the particular case of the patient, with the help of the function keys 56 or any other control device connected to the stimulator by line 67, during the performance of the treatment, as a function of the reactions of the patient to the stimulation parameters proposed by the initial program.

The presence, on the stimulator, of the function keys 56 subordinate to the software, enables the user to juggle between the serving cards and the patient cards and to personalise the chosen program at will, without requiring a connection to an external control unit. The advantages of such a design are obvious, since they confer the appliance with great adaptability, which provide a great comfort in use.

Of course it is also possible to personalise the programs by using any personal computer equipped with a standard RS-232C serial link, and which is connected to the stimulator by means of cable 67, and even to perform totally free programming, by using programs prepared for this purpose and supplied on diskettes 68.

The software uses adequate interpolation functions, such as, for example, spline functions (variable degree polynomials functions of Chebyshev, Lagrange, Spline, etc.) which allow the calculation of a variation curve of the value of the parameter between the various successive samplings, so that this value follows a harmoniously progressive and smoothed curve. Thus, the device has the advantage of allowing a controlled progressive and physiological variation of the type of work imposed on the muscle and also to avoid a brutal and harmful overload of the tendino-muscular appliance.

Figure 5:
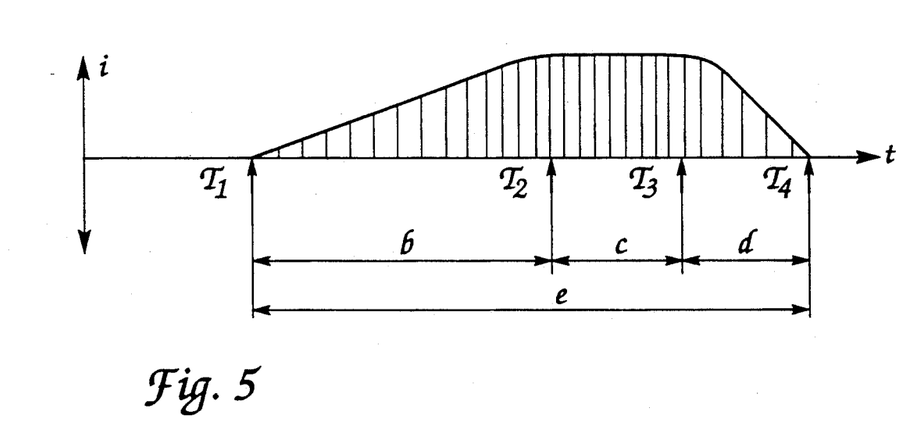
FIG. 5 is a diagram as a function of the time t of a train of impulses, comprising an establishment time and an extinction time.

A diagrammatic example of a train of impulses of duration e comprising an establishment time b and an extinction time d is shown on FIG. 5. The duration c of nominal intensity of the impulses is equal to e-b-d. This diagram also illustrates the programmable progressive variation in the frequency of the impulses, as a function of the time t of the performance of the program of treatment, between the points $T_1$ and $T_2$ (setting-up slope), then $T_3$ and $T_4$ (extinction slope) of initialisation-sampling; the value of the frequency and the smoothed envelope curve of the intensity of the impulses between these various points T being calculated by interpolation functions included in the software.

The totally computerised design of the stimulator with circuitry (hardware) of the amorphous type, entirely subordinate to the control and the monitoring of the software, enables by means of the latter to provide interactive connections between the various stimulation parameters as a function of the performance time of a program of treatment. An example of this is provided here by the subordination of the intensity of the stimulation current supplied to each output to the frequency of the electrical impulses supplied to said same output.

Figure 7:
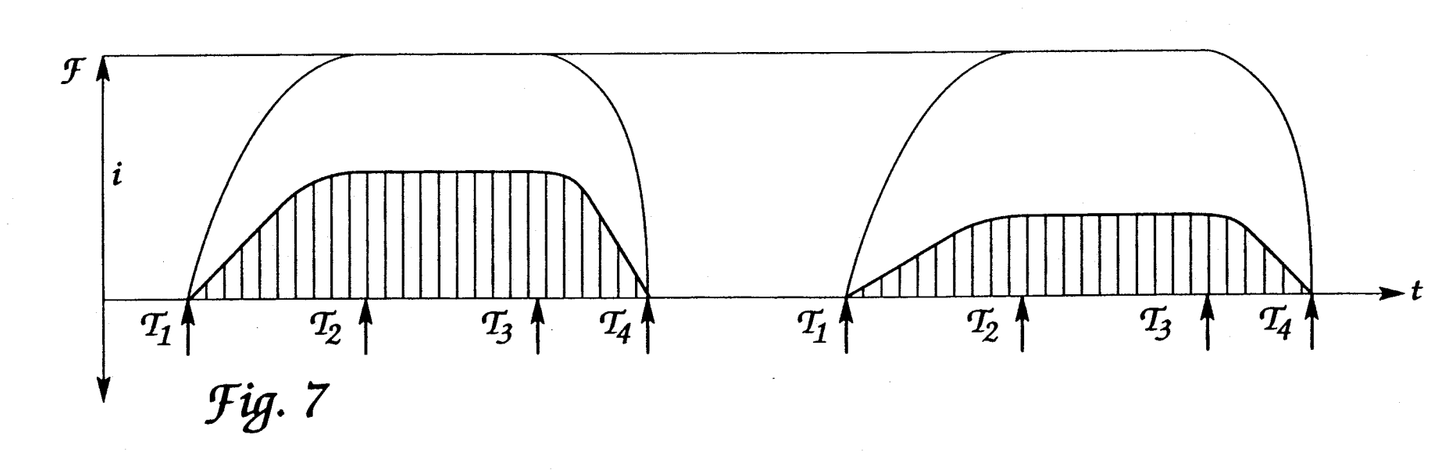
FIG. 7 is a diagram which illustrates an example of interactive parameters as a function of the time t for performing a program of treatment.

FIG. 7 shows by way of example the subordination by the program of the intensity i of the impulses as a function of the programmed variable frequency of the impulses; the result, the force F produced by the stimulated muscle is thus kept constant.

Figure 8:
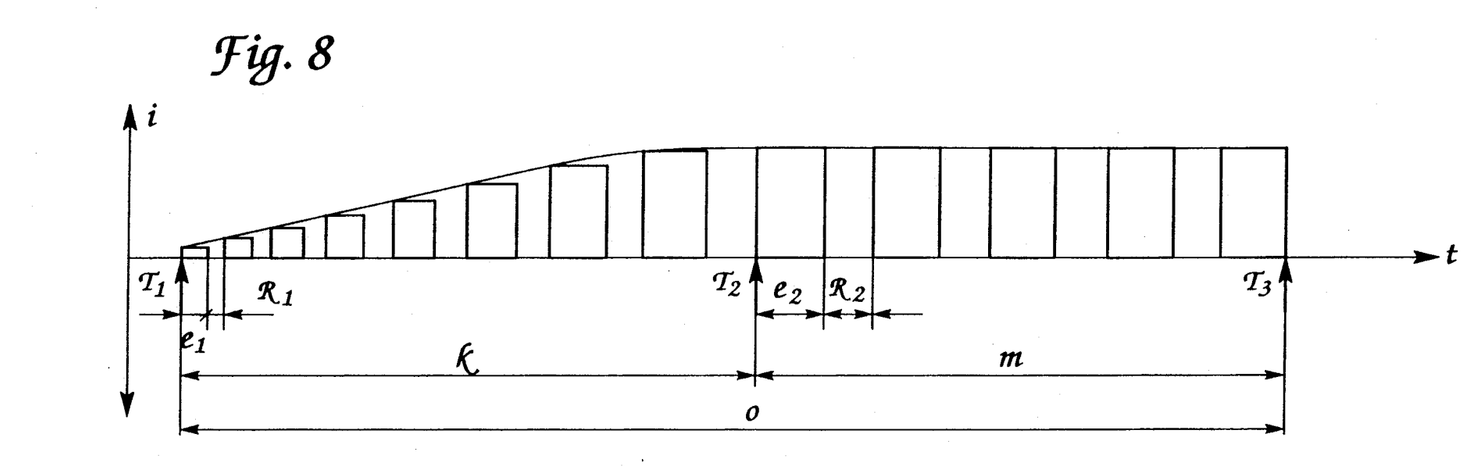
FIG. 8 is a diagram illustrating a set of trains of impulses e forming a series o.

A set of impulse trains e forming a series c is shown on FIG. 8. This diagram also illustrates an example of interactive parameters, that is to say the programmable progressive variation, as a function of the performance time t of the program of treatment, of the intensity of the stimulation current i, of the duration of the impulse trains (from $e_1$ to $e_2$) and of the duration of the pause (from $h_1$ to $h_2$) between the impulse trains, between initialisation-sampling points $T_1$, $T_2$ and $T_3$; the respective values of these parameters and the smooth envelope curve of the stimulation current i being calculated by functions of interparameter connection and of interpolation included in the software. This diagram also illustrates the set of impulse trains contained in the ramp k of series o, as well as the phase m of nominal work.

As has been stated above, the force produced by a muscle is the result of the combination of the spatial summation and the temporal summation, i.e. on the electrostimulation ground, of the combination of the intensity of the electrical impulse and of its repetition frequency. It may even be precised that for a given stimulated muscle, the force produced is equal to the product of the intensity of the current by the frequency of the impulses, multiplied by a variable experimental corrective value. This variable factor, the value of which is a function of the frequency of the impulses and of the structure of the fibers comprising the respective muscle, may be determined by means of a correlation table drawn up in an experimental manner and precised for each muscle by a simple initialisation procedure.

As a matter of fact it should be remembered that the type I fibers show a complete tetanisation at approximately 25 Hertz, whereas this same complete tetanisation is only achieved at around 50 to 65 Hertz for type II fibers. As the different skeletal muscles contain variable proportions of these different types of muscular fibers and moreover this proportion varies from one individual to another, it is obvious that it is scarcely possible to draw up a single correlation table which guarantees an acceptable general approximation of the variable factor indicated above. However this drawback may be easily overcome by a very simple initialisation procedure carried out prior to the treatment: the stimulator acting on the respective patient is loaded with the program of treatment. With the use of the programming computer connected by its serial on-line link or by means of function keys, the therapist then successively applies to each output (pair of electrodes) the following procedure: he supplies a subtetanic impulse frequency in the order of 8–10 Hertz and raises the intensity of the stimulation current to the maximum tolerance threshold of the subject; this data is then memorised by the program, then the intensity of the current is brought back to zero, the frequency is increased to 50–65 Hertz and the therapist again raises the current intensity to the maximum threshold tolerated by the patient, with this data in turn being memorised by the program. The latter may therefore calculate, by an adequate interpolation function and with the use of the above-mentioned correlation table, the subordination of the intensity of the stimulation current by the frequency of the impulses, in such a way that the force produced by the stimulated muscle remains constant when the programmed frequency of the impulses varies as a funcion of the progress of the program of treatment.

What has just been described above obviously implies that the adjustment of the intensity of the stimulation current as a function of the performance time of the program of the treatment is monitored by the programming software.

Moreover, the intensity of the stimulation current supplied to each output is automatically and systematically registered and memorised by the software as a function of the performance time of the program of treatment. The intensity thus memorised will automatically be restored at the occasion of a subsequent application of said program of treatment, throughout its performance.

Although, as described above, the intensity is subordinate to the programmed frequency of the impulses, the patient nevertheless retains at any time the possibility to alter this intensity, purely manually, by means of the control key provided for this purpose. The new intensity thus assigned by the patient is in turn recorded and memorised and the interpolation functions described above then automatically recalculate the new curve of the values of this parameter as a function of the performance time of the program of treatment.

In the example described here, the stimulator comprise four outputs, which are electrically independent, insulated galvanically from one another and the earth, and consequently called "floating". The programming and the operating of each output, as a function of the performance time of a program of treatment, are totally independent. They may however be coupled interactively by the connections provided by the software between the different stimulation parameters as a function of the performance time of the program of treatment, as described above. As a matter of fact, this interactive coupling of the parameters is also possible between the parameters of the different output channels.

Figure 10:
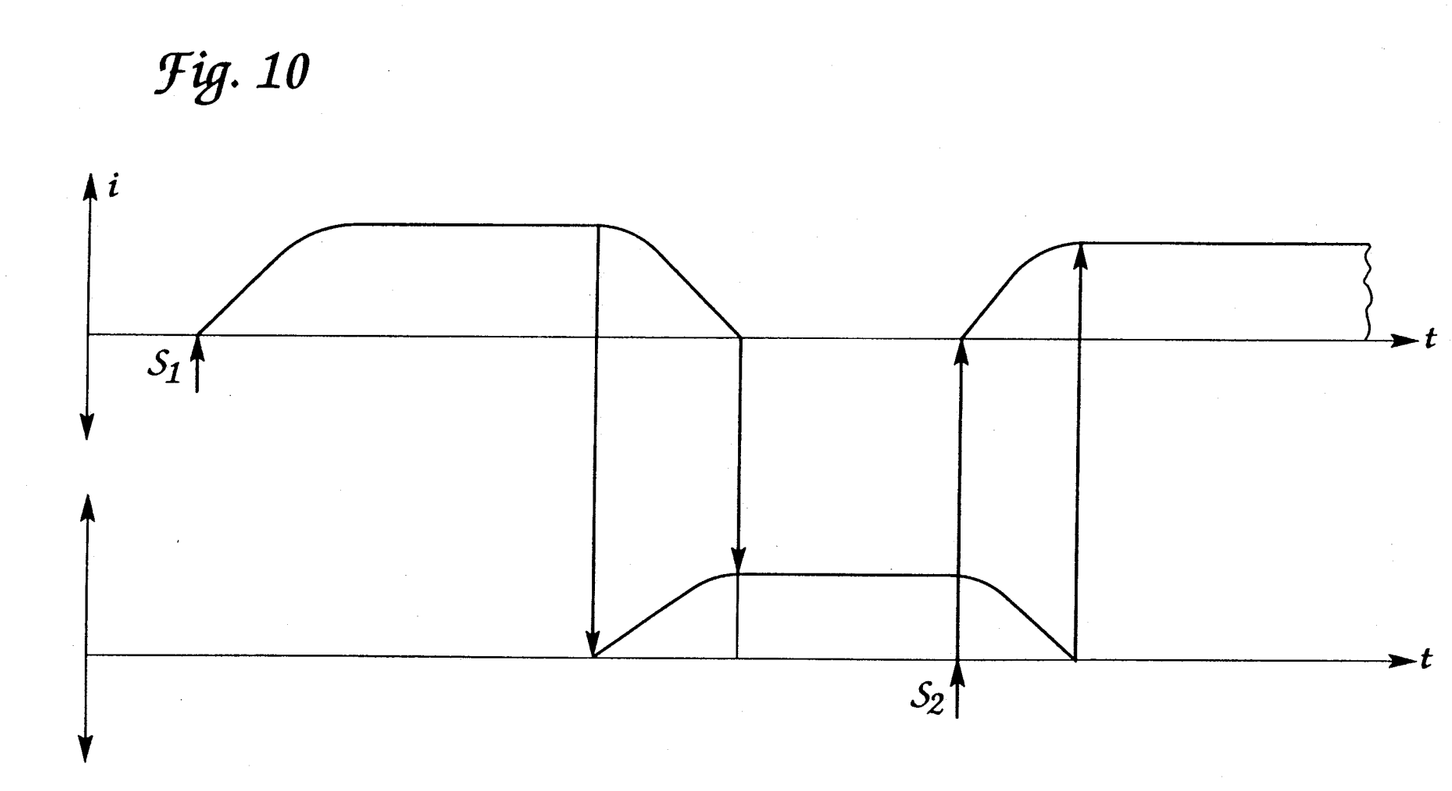
FIG. 10 is a diagram which illustrates an example of external control and interactive parameters between two distinct output channels, as a function of the time t for performing the program of treatment.

One example of external control and interactive parameters between two distinct output channels, as a function of the performance time t of the program of treatment is shown on the diagram of FIG. 10. The individual external control $S_1$ of the first channel determines the start of a first train of impulses; the end thereof controls the establishment of a train of impulses of the second channel; this train of impulses is interrupted by the individual external control $S_2$ of this second channel; the end of this latter train of impulses thus controls the establishment of a new train of impulses of the first channel.

Figure 4:
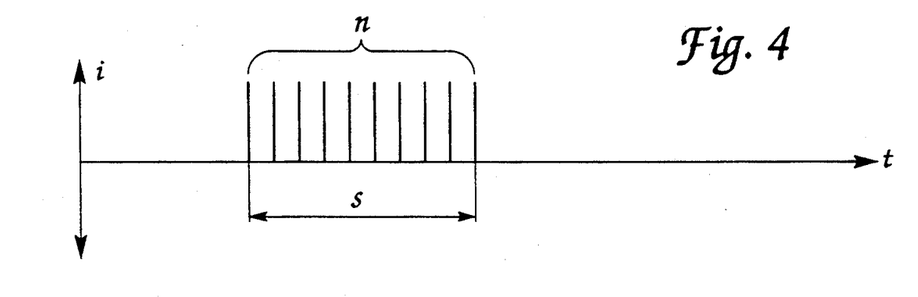
FIG. 4 illustrates the repetition frequency of impulses as a function of the time t, expressed in Hertz, that is to say the number n of impulses per second s.
Figure 6:
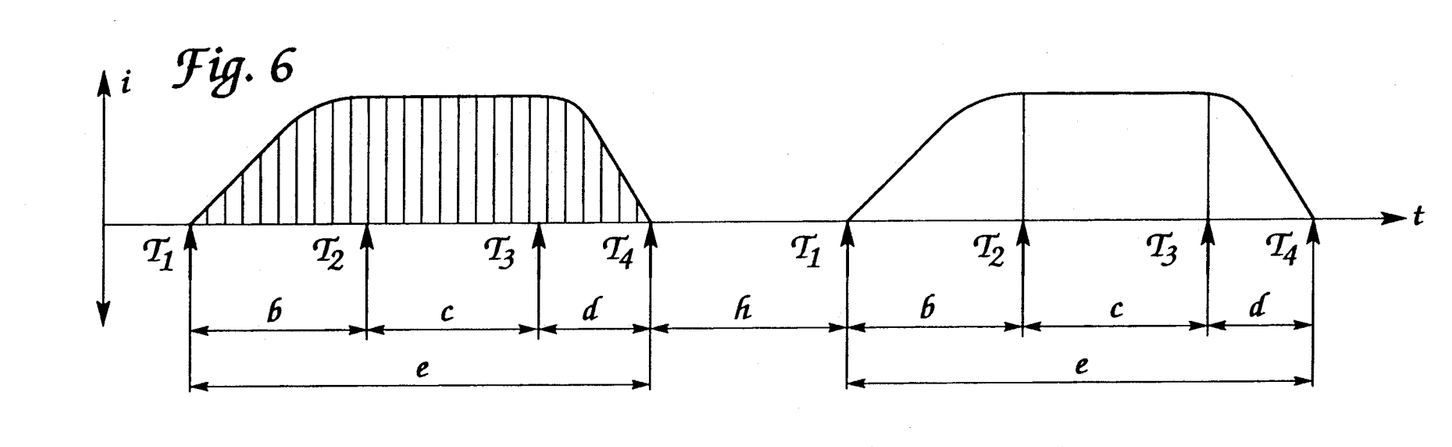
FIG. 6 illustrates two consecutive trains of impulses and the pause of duration h which separates these two trains.
Figure 9:
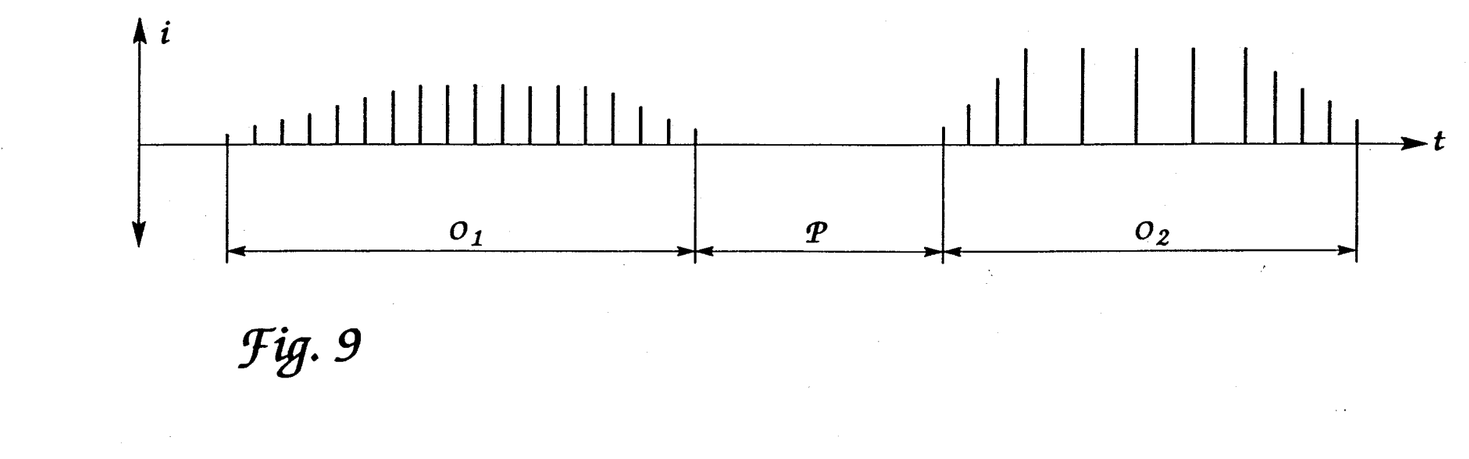
FIG. 9 illustrates two consecutive series $o_1$ and $o_2$ and the period p characterising an interval between two consecutive series.

The main stimulation parameters are as follows:
the form of the electric impulse, that is to say the variation of its amplitude as a function of its duration (FIG. 3),
the duration a, a' of the impulse,
the amplitude i of the impulse,
the repetition frequency of the impulses as a function of time (FIG. 4),
the duration e of a train of impulses (FIG. 5),
the duration h of the pause which separates two trains of consecutive impulses (FIG. 6),
the time b or the establishment slope of a train of impulses (FIG. 5),
the time d or the extinction slope of a train of impulses (FIG. 5),
the duration or the number characterising a set of trains of impulses forming a series o (FIG. 8),
the period p characterising an interval between two consecutive series (FIG. 9),
the duration or the number characterising a set of trains of impulses contained in the ramp k of a series (FIG. 8),
the duration of the program of treatment.

The above list does not claim to be exhaustive, as it is true that other parameters may be constantly incorporated in the program at will, as required.

It is known that the optimal parameters for stimulating and monitoring the progress of a program of treatment vary greatly as a function of the particular activity projects which the therapist wishes to impose on the muscles, in agreement with its therapeutic objectives, which ar specific to each case and to each patient, and that these parameters moreover evolve constantly as a function of the continuous progress in the knowledge of the modern physiology of the muscle.

The design of the device of the present invention, designed with an amorphus circuitry (hardware), entirely under the control of programs (software), formulated to enable a freely developing dynamic programming with interactive parameters, enables any possible planned interactive projects for muscular activities to be programmed, at will and in a completely evolutionary way, moreover by offering the choice of an aerobic, anaerobic alactic or anaerobic lactic metabolism, however complex they may be, whilst guaranteeing the patient an application which is one of the simplest, because of the integral automation of the performance of the program of treatment, one of the safest, because of the safety devices described (interpolation and initialisation functions), and one of the most reliable, because of an absolute and unavoidable observance.

As described above, the device of the invention enables both all the treatments to be performed by electromyostimulation of the normally innervated peripheral muscles and peripherally enervated muscles and also the nervous stimulation treatments having an antalgic purpose, or even ionotherapy treatments (medicinal ionisation) to be performed, such as, for example:
stimulation of the healthy muscle, which is normally innervated;
stimulation of the peripherally enervated muscle;
neuro-muscular electrodiagnostic, establishment of the intensity-duration curve, rheobase, chronaxie, climalysis, dissociation of the thresholds by the Fischgold method, etc.;
antalgic stimulation with anti-familiarisation wobulation of the signal;
ionotherapy (medicinal ionisation by controlled direct current);
training of all functional, even complex, activity, thanks to four output channels, which can be programmed independently of one another, and thanks to the modular design of the device, with data bus which enables the interactive remote control of the output channels of one or several stimulators connected in network;
etc.

Observance or compliance with the treatment consists in a retrocontrol of the correct performance of the treatment program by the patient. This retrocontrol of certain significant parameters of the said treatment, such as its duration, its intensity, etc., is defined by the software and it is memorised on the detachable and interchangeable information medium connected to the stimulator. This constant observance may thus at any time be reread and interpreted by the therapist. Reliable observance is an essential element of the prscribed treatment, as much to guarantee the credibility of the clinical studies as to reassure the payers, normally the insurers, that the appliances are properly used by the patients at home.

Some stimulators equipped with some type of observance device are already known. However, the devices proposed can far too easily be distorted by the patient, since all he has to do is perform a simple short-circuit of each pair of electrodes (without placing them on his body) to elude observance and to thus give the therapist the illusion of having perfectly performed his program of treatment.

The resolution of this problem is complex as the shortcircuit impedance of the electrodes is in fact very close to that revealed under body weight during an electrical stimulation impulse. As a matter of fact, for physiological reasons, the mean duration of such an impulse is in the order of just 300 microseconds for the stimulation of normally innervated muscles. The use of such a short duration enables, inter alia, an essentially transcutaneous passage of the current by capacitive effect rather than ohmic effect, by only a low impedance opposing it.

The device of the present invention guarantees a reliable solution to this problem. The impedance of the charge between a pair of electrodes is constantly measured throughout treatment. If its value exceeds a limit value, assigned by the software, the stimulation current is automatically interrupted and a specific symbol is displayed on the LCD monitoring screen of the stimulator. This device enables harmful effects of any poor contact to be detected and eliminated, as much at the level of the connectors, cables, electrodes, as of the skin itself. Consequently, if there is no charge between the electrodes, it is obvious that the treatment can not be commenced.

Moreover, when the user operates the start key for a program of treatment, prior to the start of the stimulation in the true sense of the word, the device generates between the electrodes an impulse of constant current which lasts some milliseconds, but with a very weak current intensity, largely subliminal with respect to the sensitiveness threshold of the patient. As the constant current of this impulse charges the cutaneous capacity at the level of the electrodes, it follows that the voltage necessary to supply this impulse increases progressively along a certain slope. It will be recalled that if the charge between the electrodes is a purely ohmic resistance, the voltage then remains constant. It is therefore sufficient to compare the value introduced into the software, so that the latter decides whether to perform the start of the program of treatment or not. The advantage of this device is that it prevents not only the short-circuiting of the electrodes, but also the use of a simple artificial load with ohmic resistance. As a matter of fact it only accepts a combined ohmic-capacitive load close to a real corporal load.

I claim:

1. An electrical neuromuscular stimulation device, comprising at least one autonomous portable stimulation unit equipped with at least one output with at least one pair of electrodes to be applied to the part of a patient's body to be treated that are in electrical communication with electronic circuitry means that transmit trains of electrical stimulation impulses intended to cause contractions and muscular exercise or training through said electrodes, and software control means that controls and supervises the transmission of said trains of electrical stimulation impulses, including detachable and interchangeable information medium previously programmed as a function of the stimulation treatment parameters for individual patients and further including first means for enabling the value of each parameter of the stimulation treatment to evolve progressively between previously programmed reference values, and second means for enabling any parameter of stimulation treatment to control any other parameter of stimulation treatment.

2. A device according to claim 1 wherein the stimulation unit further comprises electrical impulse generating microprocessor means for enabling the value of any stimulation parameter to evolve in a continuous and progressive manner among previously assigned reference values, while any given parameter may control another parameter, as a function of the performance time of the program of treatment.

3. A device according to claim 2 wherein the microprocessor means calculates and supplies high frequency impulses to a first insulation cell comprising an output pulse shaper-amplifier of the stimulation current transmitted towards said electrodes, so as to form a rectifier stage, with the insulation cell being supplemented by an electronic polarity change-over switch stage that is controlled by the software control means through a second insulation cell.

4. A device according to claim 3 and further including means to progressively adapt the electrical impulses generated by the microprocessor means to cause consecutive series of muscular contractions, which enable the selection of an energetic aerobic, anaerobic alactic or anaerobic lactic metabolism.

5. A device according to claim 4 wherein the stimulation unit further comprises means subordinate to the software control means and to the microprocessor means for interrelating the different stimulation treatment parameters to make them interactive as a function of the automatic progress of the program of treatment, and in particular to make them interactive as a function of the automatic progress of the program of treatment, and in particular to make the intensity of the stimulation current subordinate to the frequency of the electrical impulses supplied, so as to ensure physiological muscular work and without any risk for the tendino-muscular appliance.

6. A device according to one of claims 2 to 5 wherein the stimulation unit is equipped with four outputs which are not electrically interconnected but which can be interrelated interactively by the connections specified by the software control means between the different stimulation treatment parameters as a function of the performance time of the program of treatment.

7. A device according to claim 6, and further comprising means for a data bus type connection for the external interactive control of the output channels of a plurality of stimulator units connected in network.

8. A device according to claim 7 wherein the stimulation unit further comprises a matrix dot LCD screen controlled by the software control means and second software means, providing the program of treatment, so as to enable the monitoring of all the functions of the device and of the stimulation, the stimulation unit further comprising function key means subordinate to the second software means enabling the program of treatment to be personalised, said screen and said function key means being disposed on a unit having means that fold down to form a protective cover.

9. A device according to claim 8, wherein said information medium further comprises program-cards preprogrammed with standard programs of treatment, each program being specific to a precise medical indication, and means to allow the user of the device to choose one of the programs of treatment, on a patient program-card which he introduces including a slot provided in said stimulation unit that is equipped with a connector for receiving said program-cards.

10. A device according to claim 9 wherein the stimulation unit further comprises means subordinate to the software control means and to the microprocessor means for memorising the intensity of the electrical stimulation current assigned by a therapist or by the patient and supplied to the electrodes as a function of the automatic progress of the program of treatment, and means to then progressively restore the same intensity at the time of a subsequent treatment, the stimulation unit further comprising means subordinate to the software control means and to the microprocessor means designed to monitor the observance of the treatment by the patient by measuring constantly the impedance of the charge between the two electrodes of each pair of electrodes throughout the entire treatment and by carrying out a preliminary test measurement by generating a constant current impulse of a subliminal intensity and of an adequate duration to allow the comparison of the voltage slope of this signal with a preprogrammed value, the stimulation unit further comprising safety means which can be operated by the patient to adjust exclusively the intensity of the stimulation within programmed units.

11. A device according to claim 3 wherein the stimulation unit further comprises means subordinate to the software control means and to the microprocessor means for interrelating the different stimulation treatment parameters to make them interactive as a function of the automatic progress of the program of treatment, and in particular to make the intensity of the stimulation current subordinate to the frequency of the electrical impulses supplied, so as to ensure physiological muscular work and without any risk for the tendino-muscular appliance.

12. A device according to claim 2 wherein the stimulation unit further comprises means subordinate to the software control means and to the microprocessor means for interrelating the different stimulation treatment parameters to make them interactive as a function of the automatic progress of the program of treatment, and in particular to make the intensity of the stimulation current subordinate to the frequency of the electrical impulses supplied, so as to ensure physiological muscular work and without any risk for the tendino-muscular appliance.

13. A device according to claims 1 to 11 wherein each output channel includes programming means for programming each output channel independently from the others and means to allow an interdependence of their activity, with every parameter of an output channel being able to control another output channel, so as to allow the programming of multiple muscular activities.

14. A device according to claim 2 wherein the stimulation unit further comprises means subordinate to the software control means and to the microprocessor means for memorising the intensity of the electrical stimulation current assigned by a therapist or by the patient and supplied to said electrodes as a function of the automatic progress of the program of treatment, and means to then progressively restore the same intensity at the time of a subsequent treatment.

15. A device according to one of claims 2 or 14 wherein the stimulation unit further comprises means subordinate to the software control means and to the microprocessor means to monitor the observance of the treatment by the patient by measuring constantly the impedance of the charge between the two electrodes of each pair of electrodes throughout the entire treatment and by carrying out a preliminary test measurement by generating a constant current impulse of a subliminal intensity and of an adequate duration to allow the comparison of the voltage slope of this signal with a preprogrammed value.

16. A device according to claim 1 wherein the stimulation unit further comprises safety means which can be operated by the patient to adjust exclusively the intensity of the stimulation within programmed limits.

17. A device according to claim 1 wherein the stimulation unit further comprises a matrix dot LCD screen controlled by the software control means an second software means, providing the program of treatment, so as to enable the monitoring of all the functions of the device and of the stimulation.

18. A device according to claim 17 wherein the stimulation unit further comprises function key means subordinate to the second software means enabling the program of treatment to be personalized.

19. A device according to claim 18, wherein the screen and the function key means are disposed on a unit having means that down to form a protective cover.

20. A device according to claim 1 wherein the stimulation unit further comprises a slot within said stimulation unit equipped with a connector for receiving said program-cards.

21. A device according to claim 20, wherein said information medium further comprises program-cards preprogrammed with standard programs of treatment, each program being specific to a precise medical indication, and means to allow the user of the device to choose one of the programs of treatment including introducing a program-card into the slot by replacing the previously established program-card.

22. A device according to claim 21 wherein the stimulation unit includes a connector in electrical communication with said electronic circuitry means and having a detachable cable fitted with an RS-232C type serial link, whereby said cable may be connected to a computer.

23. A device according to claim 21 wherein the stimulation unit further comprises a multi-function connector in electrical communication with said electronic circuitry means whereby the stimulator unit may be connected to a battery charger, an auxiliary power supply battery, and to peripheral control unit.

24. A device according to claim 23, and further comprising means providing for a data bus type connection for the external interactive control of the output channels of a plurality of stimulation units connected in network.

25. An electrical neuromuscular stimulation device, comprising at least one autonomous portable stimulation unit equipped with at least one output with at least one pair of electrodes to be applied to the part of a patient's body to be treated that are in electrical contact with a microprocessor having electronic circuitry means that transmit trains of electrical stimulation impulses intended to cause contractions and muscular exercise or training through said electrodes, and software control means that controls and supervises the transmission of said trains of electrical stimulation impulses, including detachable and interchangeable information medium previously programmed as a function of the stimulation treatment parameters for individual patients and means for enabling the value of each parameter of the stimulation treatment to evolve progressively throughout the program between previously programmed reference values, and second means for enabling any parameter to control another parameter of stimulation treatment, the electronic circuitry means further comprising means for enabling the output of signals adapted for the treatment of both normally innervated muscles and peripherally enervated muscles, as well as ionotherapy.

26. A device according to claim 25 wherein the microprocessor calculates and supplies high frequency impulses to an insulation cell comprising an output pulse shaper-amplifier of the stimulation current transmitted towards said electrodes, so as to form a rectifier stage, with the insulation cell being supplemented by an electronic polarity change-over switch stage that is controlled by the software control means, through a second insulation cell.

27. A device according to claim 26 wherein the stimulation unit further comprises a matrix dot LCD screen and controlled by the software control means and second software means providing the program of treatment, so as to enable the monitoring of all the functions of the device and of the stimulation, the stimulation unit further comprising function key means subordinate to the second software means enabling the program of treatment to be personalised, said screen and said function key means being disposed on a unit having means that fold down to form a protective cover.

28. An electrical neuromuscular stimulation device, comprising at least one autonomous portable stimulation unit equipped with at least one output with at least one pair of electrodes to be applied to the part of a patient's body to be treated that are in electrical contact with electronic circuitry means that transmit trains of electrical stimulation impulses intended to cause contractions and muscular exercise or training through said electrodes, and software control means that controls and supervises the transmission of said trains of electrical stimulation impulses, comprising means for ensuring an interaction of the parameters of the stimulation impulses and a linkage of said parameters by interrelation and interaction functions, with said software control means being memorised on detachable information medium, and means for enabling the value of each parameter of the stimulation impulses to evolve progressively throughout the program between previously programmed reference values, and means for enabling any parameter to control another parameter, the stimulation unit further comprising a matrix dot LCD screen controlled by the software control means and second software means providing the program of treatment, so as to enable the monitoring of all the functions of the device and of the stimulation, the stimulation unit further comprising function key means subordinate to the second software means enabling the program to be personalised, said screen and said function key means being disposed on a unit having means that fold down to form a protective cover.

* * * * *

UNITED STATES PATENT AND TRADEMARK OFFICE
CERTIFICATE OF CORRECTION

PATENT NO. : 5,285,781   Page 1 of 2

DATED : February 15, 1994

INVENTOR(S) : Roland Brodard

It is certified that error appears in the above-identified patent and that said Letters Patent is hereby corrected as shown below:

Title page, col. 2, immediately before the Abstract, the following law firm is to be listed as the "Attorney, Agent or Firm": -- Woodard, Emhardt, Naughton, Moriarty & McNett --.

In the Abstract, line 1, after the word "stimulation" insert the word -- device, --.

In column 16, lines 11-13, delete the words "them interactive as a function of the automatic progress of the program of treatment, and in particular to make".

In column 16, lines 45-46, delete the words "on a patient program-card which he introduces--.

In column 17, line 3, change "units" to -- limits --.

In column 17, line 26, change "1 to 11" to --1 to 5 and 11 to 12 --.

In column 17, line 61, change "an" to -- and --.

UNITED STATES PATENT AND TRADEMARK OFFICE
CERTIFICATE OF CORRECTION

PATENT NO. : 5,285,781
DATED : February 15, 1994
INVENTOR(S) : Roland Brodard

It is certified that error appears in the above-identified patent and that said Letters Patent is hereby corrected as shown below:

In column 18, line 3, between the words "that" and "down" insert the word -- fold --.

In column 18, line 27, change "unit" to -- units --.

Signed and Sealed this

Twentieth Day of September, 1994

Attest:

BRUCE LEHMAN

Attesting Officer

Commissioner of Patents and Trademarks